United States Patent
Herold et al.

(10) Patent No.: US 6,800,781 B2
(45) Date of Patent: Oct. 5, 2004

(54) PROCESS FOR QUENCHING A GASEOUS REACTION MIXTURE DURING THE GAS PHASE PHOSGENATION OF DIAMINES

(75) Inventors: Heiko Herold, Neuss (DE); Herbert Stutz, Dormagen (DE); Hans-Joachim Brockhaus, Leverkusen (DE); Volker Michele, Köln (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 10/670,409

(22) Filed: Sep. 25, 2003

(65) Prior Publication Data

US 2004/0068137 A1 Apr. 8, 2004

(30) Foreign Application Priority Data

Sep. 30, 2002 (DE) ......................................... 102 45 704

(51) Int. Cl.[7] ............................................. C07C 263/00
(52) U.S. Cl. ........................ 560/347; 560/352; 560/359
(58) Field of Search ............................... 560/347, 352, 560/359

(56) References Cited

U.S. PATENT DOCUMENTS

| | | | | |
|---|---|---|---|---|
| 4,847,408 A | * | 7/1989 | Frosch et al. | ................ 560/347 |
| 5,449,818 A | * | 9/1995 | Biskup et al. | ............... 560/347 |
| 5,633,396 A | | 5/1997 | Bischof et al. | ............. 560/374 |

* cited by examiner

*Primary Examiner*—Rita Desai
*Assistant Examiner*—Hector M. Reyes
(74) *Attorney, Agent, or Firm*—Joseph C. Gil; John E. Mrozinski, Jr.

(57) ABSTRACT

The present invention provides a process for quenching a gaseous reaction mixture during the phosgenation of diamines in the gas phase to produce diisocyanates. The gaseous reaction mixture contains at least a diisocyanate, phosgene and hydrogen chloride. The quenching liquid is injected into the gas mixture continuously flowing out of a cylindrical reaction zone into the downstream cylindrical quenching zone with the aid of at least two spray nozzles which are arranged at the entrance to the quenching zone at equal distances along the circumference of the quenching zone.

11 Claims, 2 Drawing Sheets

PROCESS FOR QUENCHING A GASEOUS REACTION MIXTURE DURING THE GAS PHASE PHOSGENATION OF DIAMINES

FIELD OF THE INVENTION

The present invention provides a process for quenching a gaseous reaction mixture during the phosgenation of diamines in the gas phase to produce diisocyanates, wherein the gas mixture contains at least diisocyanate, phosgene and hydrogen chloride. Quenching is achieved by injecting a quenching liquid into the gas mixture.

BACKGROUND OF THE INVENTION

The preparation of diisocyanates by reacting diamines with phosgene in the gas phase is described, for example, in EP 0 289 840. The diisocyanates formed in a cylindrical reaction chamber, such as a tubular reactor, are not thermally stable at the reaction temperatures of 300 to 500° C. Rapid cooling of the reaction gases after the phosgenation reaction to temperatures below 150° C. is therefore needed to avoid the formation of undesired secondary products due to the thermal decomposition of diisocyanate or by further reaction. For this purpose, in EP 0 289 840, the gaseous mixture continually leaving the reaction chamber, which contains, inter alia, diisocyanate, phosgene and hydrogen chloride, is passed into an inert solvent, e.g. dichlorobenzene. The disadvantage of this process is that the rate of flow at which the gas mixture is passed through the solvent bath has to be relatively low because at too high rates of flow the solvent and the compounds dissolved therein would be carried over. In a subsequent step, the liquid compounds have to be separated from the gas. Another disadvantage is that, due to the low rates of flow and a small heat transfer term, large solvent containers have to be used to produce the cooling effect.

Furthermore, processes are known which use heat exchangers and/or expand the gases into a vacuum to cool the reaction gases. The disadvantage of heat exchangers is that, due to poor heat transfer, large exchange surfaces and thus large heat exchangers are required for effective cooling. In addition, deposits of solids on the relatively cold surfaces of the heat exchangers takes place due to secondary reactions of the gas mixture on these surfaces, such as e.g. decomposition or polymerization. The transfer of heat is further impaired by these deposits and this leads to a higher residence time and thus results in a further increase in secondary product formation. On top of that, undesired shutdown times are produced for the entire plant due to cleaning of the cooling stage.

SUMMARY OF THE INVENTION

The present invention reduces or eliminates the disadvantages inherent in the art such as those mentioned above when rapidly cooling the gaseous reaction mixture present during the gas phase phosgenation of diamines to produce diisocyanates to a temperature at which the relevant reaction product is thermally stable. At the same time, the formation of undesired secondary products is suppressed.

BRIEF DESCRIPTION OF THE FIGURES

The present invention will now be described for purposes of illustration and not limitation in conjunction with the figures, wherein.

DETAILED DESCRIPTION OF THE INVENTION

Figure 1:
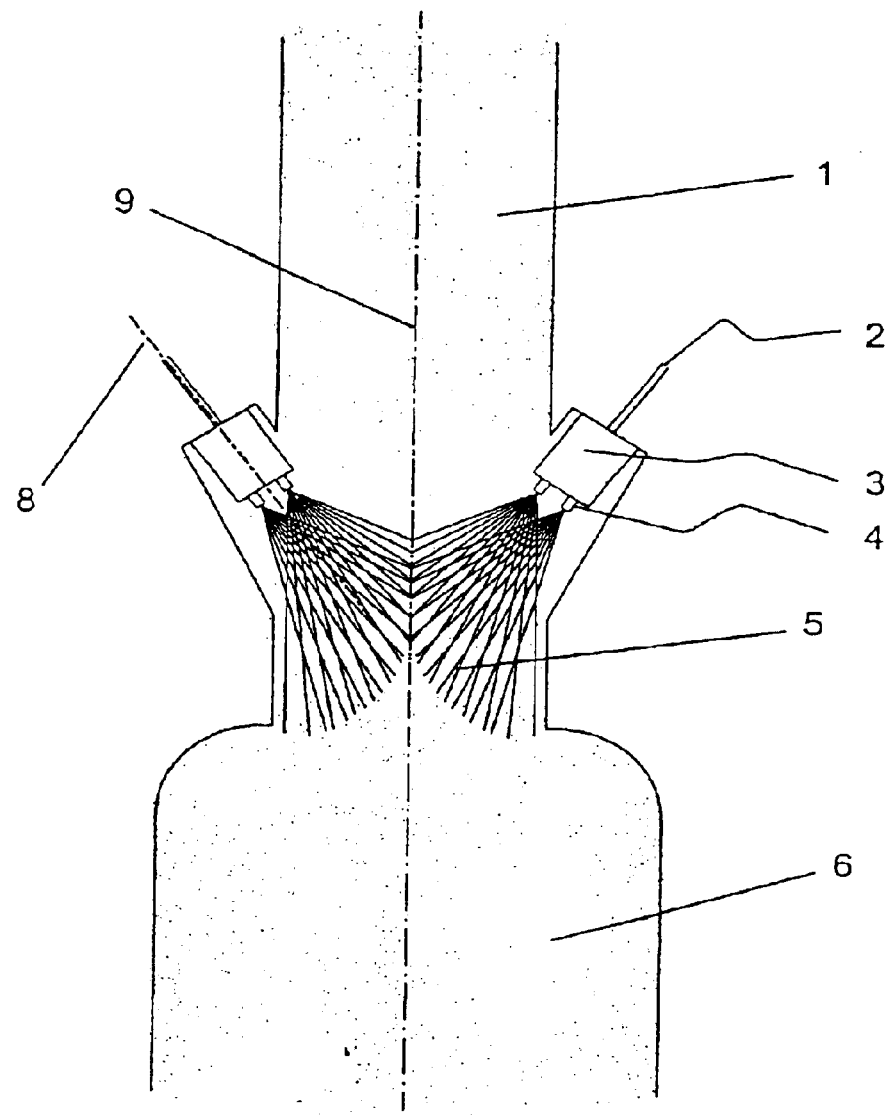
FIG. 1 shows a schematic cross-section through a first embodiment of the quenching zone.

The present invention will now be described for purposes of illustration and not limitation. Except in the operating examples, or where otherwise indicated, all numbers expressing quantities, percentages and so forth in the specification are to be understood as being modified in all instances by the term "about."

The present invention provides a process for quenching a gaseous reaction mixture during the phosgenation of diamines in the gas phase to produce diisocyanates, wherein the gaseous reaction mixture contains at least a diisocyanate, phosgene and hydrogen chloride, by injecting a quenching liquid into the gas mixture continuously flowing out of a cylindrical reaction zone into the downstream cylindrical quenching zone, wherein the quenching liquid is injected with the aid of at least two spray nozzles arranged at the entrance to the quenching zone at equal distances along the circumference of the quenching zone.

In addition to phosgene, hydrogen chloride and the major product, diisocyanate, the gaseous reaction mixture may also contain further isocyanates produced as secondary products, as well as nitrogen and/or organic solvent.

Examples of diisocyanates prepared by the gas phase phosgenation of diamines include, but are not limited to, hexamethylene diisocyanate (HDI), isophorone diisocyanate (IPDI), naphthylene diisocyanate (NDI), toluene diisocyanate (TDI), dipenylmethane diisocyanate and dicyclohexylmethane diisocyanate (HMDI).

One advantage of the process according to the present invention is that the desired rapid cooling of the gas mixture which contains a diisocyanate, hydrogen chloride and excess phosgene from 300 to 400° C. to a maximum of 150° C. on leaving the reactor is produced by the spraying of a suitable quenching liquid. The contact time during which cooling takes place is reduced to from 0.2 to 3 s.

Spraying of the liquid is performed with conventional spray nozzles or via openings, such as slits or holes, at the exit from the reaction zone or the entrance to the quenching zone. If only two spray nozzles are provided, these are preferably arranged diametrically opposite to each other. The spray nozzles may preferably be individual nozzles. More preferably, however, nozzle heads, each with at least two individual nozzles, are used, wherein single substance nozzles are preferably chosen.

Another advantage of the process of the present invention is that the quenching liquid is sprayed into the gas stream in such a way that the hot reaction gas does not make contact with the relatively cold surfaces of the quenching zone or the nozzles and their pipes. Only after the gas mixture has cooled to the stable temperature range for the particular diisocyanate does it come into contact with the relatively cold walls of the quenching zone or other components.

The spray nozzles are preferably arranged independently of each other in such a way that the direction of flow of each quenching liquid is preferably at an angle of 0° to 50°, more preferably 20° to 35°, to the direction of flow of the gas mixture. The direction of flow of the gas mixture is substantially along the axis of the cylindrical reaction zone or of the quenching zone. If the tubular reactor is arranged in an upright position, the gas flows from top to bottom through the reaction zone and the downstream quenching zone. In the same way, the direction of flow of the quenching liquid is along the axis of the spray nozzle. The cone angle of the spray nozzles, independently of each other, is preferably 20° to 90°, more preferably 30° to 60°. In one embodiment, the direction of flow of all those nozzles which are arranged in one plane have the same angle to the direction of flow of the gas mixture and the same cone angle.

Suitable quenching liquids are organic solvents or a mixture of different organic solvents which do not react with the diisocyanate formed. The choice of solvent is also determined, inter alia, by the solubility of phosgene. Suitable solvents are, for example, toluene, chlorotoluene, xylene and chloronaphthalene.

Monochlorobenzene and o-dichlorobenzene are especially suitable. A solution of the diisocyanate formed in one of these organic solvents may also be used. In this case, the proportion of solvent is preferably 40 to 90 vol. %. The temperature of the quenching liquid is preferably 100 to 170° C.

The quenching zone downstream of the cylindrical reaction zone is also cylindrical. The diameter of the quenching zone may be chosen to be substantially identical to that of the reaction zone or larger than that of the reaction zone. The reaction zone is preferably a tubular reactor without baffles.

The process according to the present invention has the further advantage that cooling of the reaction gases takes place rapidly, preferably within 0.2 to 3 s, immediately after reaction has taken place, because the gas stream flowing out of the reactor does not have to be slowed down and/or passed into a container but is passed directly through a stream of an atomized quenching liquid. In addition, the quenching zone is designed in such a way and the nozzles are mounted in such a way that the hot gas mixture does not make contact with any of the relatively cold surfaces in the quenching zone. For this purpose, for example, the diameter of the cylindrical quenching zone may be larger than the diameter of the reaction zone.

In another embodiment of the process of the present invention, quenching of the reaction gases may also take place in several steps, preferably in two steps. In this case, each quenching step includes at least two spray nozzles at equal distances along the circumference of the quenching zone. The same quenching liquids may be used in the different quenching steps. More preferably, however, in a two-step quenching process, different quenching liquids are used in the two steps, that is an organic solvent, preferably monochlorobenzene or o-dichlorobenzene, in the first step and a solution of the diisocyanate formed in the organic solvent which was used in the first quenching step in the second step. The proportion by volume of the solvent is preferably 40 to 90%.

In the following description, the process according to the present invention is explained in more detail making reference to the figures.

FIG. 1 shows a cylindrical reaction zone 1, through which the gaseous mixture flows from top to bottom along the broken line 9. On leaving reaction zone 1, the gas mixture flows through a similarly cylindrical quenching zone 5. In the quenching zone 5 there are two nozzle heads 3, each with two individual nozzles 4, located diametrically opposite to each other. The quenching liquid is supplied to nozzle head 3 via a pipe 2. Nozzles 4 and nozzle head 3 preferably are arranged so that the direction of flow of the quenching liquid (shown by broken line 8) and that of the gas stream 9 are at an angle of 0° to 50°, more preferably 20° to 35°, to each other and thus the hot gas mixture does not make contact with the colder nozzles and nozzle head. In the quenching zone 5, cooling of the reaction gas takes place by evaporation of the atomized liquid. The remaining liquid and the cooled reaction gas pass into the liquid collection container 6 located below the quenching zone, this container acting simultaneously as a pump-tank and as apparatus to separate gas and liquid.

Figure 2:
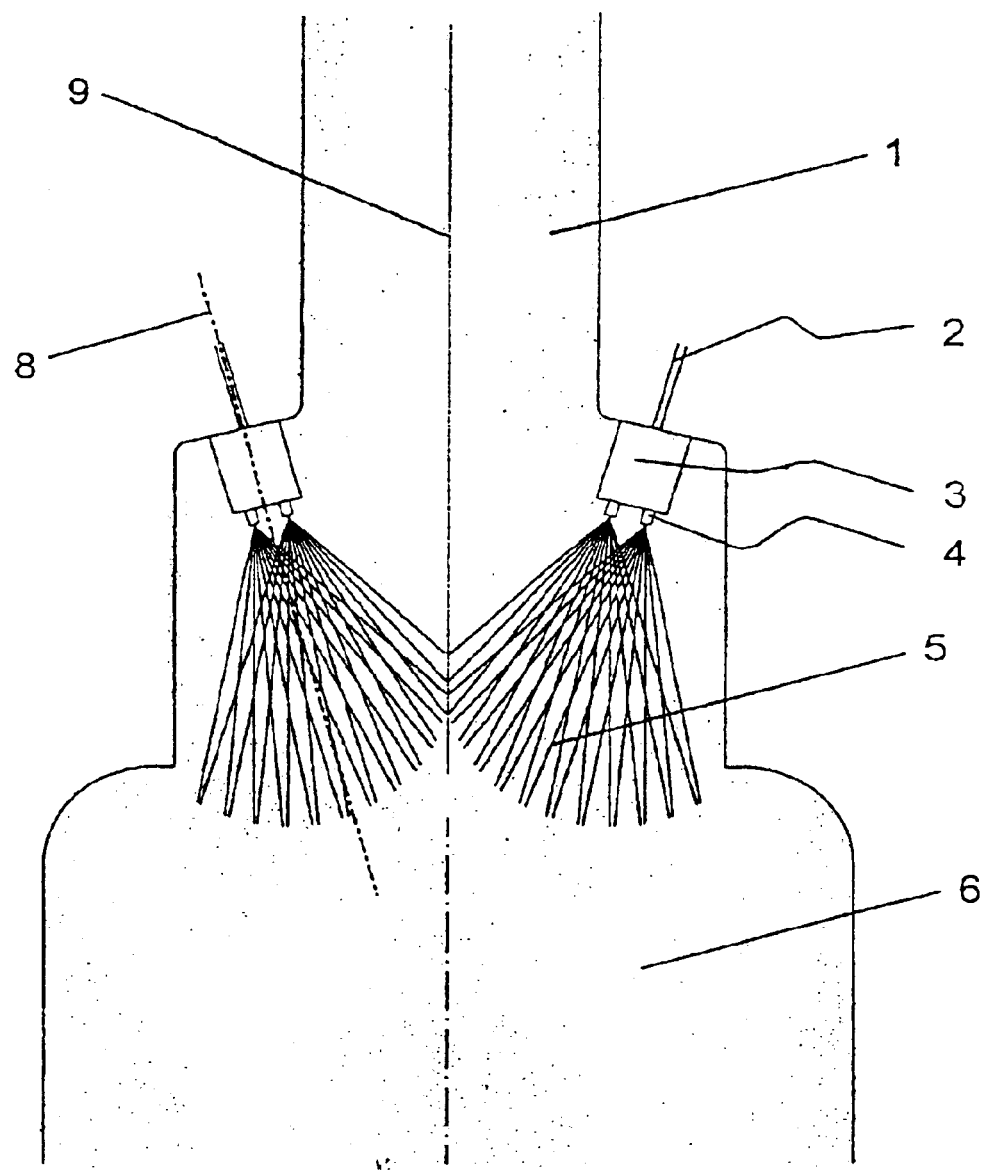
FIG. 2 illustrates a schematic cross-section through a second embodiment of the quenching zone.

The embodiment of the quenching zone shown in FIG. 2 corresponds in principle to the embodiment shown in FIG. 1. Identical or similar components therefore have the same reference numbers as in FIG. 1. The embodiment shown in FIG. 2 differs from that shown in FIG. 1 in that the diameter of the quenching zone 5 is greater than that of the tubular reactor 1.

EXAMPLE

Out of a vertically arranged tubular reactor with a diameter of 260 mm flowed 6700 kg/h of a gas mixture of isophorone diisocyanate, hydrogen chloride and excess phosgene at 400° C., at a pressure of 1000 to 1800 mbar with a speed of 18 m/s into a downstream quenching zone with a diameter of 510 mm. The tubular widening from the reactor to the quenching zone was designed with an angle of 75° to the vertical. Within the widening section, four individual nozzles were mounted at equal distances along the circumference, spraying out $130 \times 10^3$ kg/h of a solution of isophorone diisocyanate in monochlorobenzene, in a ratio by volume of 20:80, and at a temperature of 120° C. The direction of flow of the quenching liquid was at 35° to the direction of flow of the gas mixture. The cone angle of the nozzles was 30°. Cooling of the reaction gas took place in the quenching zone. The condensable constituents dissolved in the solution and the amount of monochlorobenzene required for cooling purposes evaporated. The liquid/gas mixture passed into a separator. After a contact time of 0.8 to 1.3 seconds, the temperature of the concentrated-up isophorone diisocyanate solution collected in the separator was 140° C. The gas flowing out of the separator had a temperature of 145° C.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. In a process for quenching a gaseous reaction mixture during the phosgenation of diamines in the gas phase to produce diisocyanates, in which the gaseous reaction mixture contains at least a diisocyanate, phosgene and hydrogen chloride, the improvement comprising injecting a quenching liquid into the gas mixture continuously flowing out of a cylindrical reaction zone into the downstream cylindrical quenching zone, with at least two spray nozzles arranged at the entrance to the quenching zone at equal distances along the circumference of the quenching zone.

2. The process according to claim 1, wherein the spray nozzles independently are arranged such that the direction of flow of each quenching liquid is at an angle of about 0° to about 50° to the direction of flow of the gas mixture.

3. The process according to claim 1, wherein the cone angle of the spray nozzles independently is about 20° to about 90°.

4. The process according to claim 1, wherein the spray nozzles comprise a nozzle headwith at least two individual nozzles.

5. The process according to claim 1, wherein the quenching liquid is an organic solvent, a mixture of different organic solvents or a solution of the diisocyanate in an organic solvent.

6. The process according to claim 1, wherein the temperature of the quenching liquid is about 100 to about 170° C.

7. The process according to claim 1, wherein the quenching process comprises two or more steps.

8. The process according to claim 7, wherein different quenching liquids are used in the quenching steps.

9. The process according to claim 2, wherein the angle is about 20° to about 35°.

10. The process according to claim 3, wherein the angle is about 30° to about 60°.

11. The process according to claim 1, wherein the quenching liguid is selected from the group consisting of monochlorobenzene and o-dichlorobenzene.

* * * * *